(12) United States Patent
Zhou

(10) Patent No.: US 7,597,830 B2
(45) Date of Patent: Oct. 6, 2009

(54) METHOD OF FORMING CATHETER DISTAL TIP

(75) Inventor: Pu Zhou, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 154 days.

(21) Appl. No.: 10/615,651

(22) Filed: Jul. 9, 2003

(65) Prior Publication Data

US 2005/0010194 A1    Jan. 13, 2005

(51) Int. Cl.
B29C 65/02 (2006.01)
B26D 3/16 (2006.01)

(52) U.S. Cl. .................. 264/138; 264/258; 264/259

(58) Field of Classification Search ............... 264/258, 264/134, 135; 604/523, 524, 525, 526, 527, 604/528, 529
See application file for complete search history.

(56) References Cited

U.S. PATENT DOCUMENTS

| | | | |
|---|---|---|---|
| 3,416,531 A | 12/1968 | Edwards | |
| 3,485,234 A * | 12/1969 | Stevens | ........ 600/434 |
| 3,612,058 A | 10/1971 | Ackerman | |
| 4,210,478 A | 7/1980 | Shoney | |
| 4,321,226 A | 3/1982 | Markling | |
| 4,419,095 A | 12/1983 | Nebergall et al. | |
| 4,430,083 A | 2/1984 | Ganz et al. | |
| 4,516,970 A | 5/1985 | Kaufman et al. | |
| 4,516,972 A | 5/1985 | Samson | |
| 4,531,943 A | 7/1985 | Van Tassel et al. | |
| 4,588,399 A | 5/1986 | Nebergall et al. | |
| 4,596,563 A | 6/1986 | Pande | |
| 4,636,346 A | 1/1987 | Gold et al. | |
| 4,705,511 A | 11/1987 | Kocak | |
| 4,817,613 A | 4/1989 | Jaraczewski et al. | |
| 4,842,590 A | 6/1989 | Tanabe et al. | |
| 4,863,442 A | 9/1989 | DeMello et al. | |
| 4,870,887 A | 10/1989 | Tresslar et al. | |

(Continued)

FOREIGN PATENT DOCUMENTS

EP        0 277 366 A1    8/1988

(Continued)

OTHER PUBLICATIONS

Rosato, Dominick V., Donald V. Rosato, and Marlene G. Rosato. Injection Molding Handbook (3$^{rd}$ ed.). Kluwer Academic Publishers, Boston. 2000. p. 517.*

(Continued)

*Primary Examiner*—Monica A Huson
(74) *Attorney, Agent, or Firm*—Crompton, Seager & Tufte, LLC

(57) ABSTRACT

Catheters such as guide catheters can include a reinforcing braid layer and distal tips in which the reinforcing braid layer does not extend into the distal tip. Such catheters can be formed via a process in which a first polymer segment is secured over a braid layer. The braid layer can be cut through at a cutting position that is proximate a distal end of the first polymer segment and the braid layer extending distally of the cutting position is removed. A second polymer segment that extends over the first polymer segment and that extends distally of the cutting position is secured over the braid layer.

13 Claims, 7 Drawing Sheets

U.S. PATENT DOCUMENTS

| | | | |
|---|---|---|---|
| 4,898,591 | A | 2/1990 | Jang et al. |
| 4,981,478 | A | 1/1991 | Evard et al. |
| 5,017,259 | A | 5/1991 | Kohsai |
| 5,057,092 | A | 10/1991 | Webster, Jr. |
| 5,069,674 | A | 12/1991 | Fearnot et al. |
| 5,078,702 | A | 1/1992 | Pomeranz |
| 5,160,559 | A | 11/1992 | Scovil et al. |
| 5,190,520 | A | 3/1993 | Fenton, Jr. et al. |
| 5,217,440 | A | 6/1993 | Frassica |
| 5,221,270 | A | 6/1993 | Parker |
| 5,221,372 | A | 6/1993 | Olson |
| 5,234,416 | A | 8/1993 | Macaulay et al. |
| 5,254,107 | A | 10/1993 | Soltesz |
| 5,279,596 | A | 1/1994 | Castaneda et al. |
| 5,306,252 | A | 4/1994 | Yutori et al. |
| 5,312,356 | A | 5/1994 | Engelson et al. |
| 5,335,305 | A | 8/1994 | Kosa et al. |
| 5,338,299 | A | 8/1994 | Barlow |
| 5,344,402 | A | 9/1994 | Crocker |
| 5,423,773 | A | 6/1995 | Jimenez |
| 5,433,200 | A | 7/1995 | Fleischhacker, Jr. |
| 5,454,795 | A | 10/1995 | Samson |
| 5,492,532 | A | 2/1996 | Ryan et al. |
| 5,496,294 | A | 3/1996 | Hergenrother et al. |
| 5,509,910 | A | 4/1996 | Lunn |
| 5,538,513 | A | 7/1996 | Okajima |
| 5,545,149 | A | 8/1996 | Brin et al. |
| 5,603,705 | A | 2/1997 | Berg |
| 5,662,622 | A | 9/1997 | Gore et al. |
| 5,674,208 | A | 10/1997 | Berg et al. |
| 5,695,469 | A | 12/1997 | Segal |
| 5,702,373 | A | 12/1997 | Samson |
| 5,711,909 | A | 1/1998 | Gore et al. |
| 5,755,704 | A | 5/1998 | Lunn |
| 5,759,173 | A | 6/1998 | Preissman et al. |
| 5,769,796 | A | 6/1998 | Palermo et al. |
| 5,792,124 | A | 8/1998 | Horrigan et al. |
| 5,811,043 | A | 9/1998 | Horrigan et al. |
| 5,820,612 | A | 10/1998 | Berg |
| 5,827,242 | A | 10/1998 | Follmer et al. |
| 5,836,926 | A | 11/1998 | Peterson et al. |
| 5,891,112 | A | 4/1999 | Samson |
| 5,891,114 | A | 4/1999 | Chien et al. |
| 5,906,606 | A | 5/1999 | Chee et al. |
| 5,911,715 | A | 6/1999 | Berg et al. |
| 5,947,925 | A * | 9/1999 | Ashiya et al. .......... 604/164.08 |
| 5,951,495 | A | 9/1999 | Berg et al. |
| 5,951,929 | A * | 9/1999 | Wilson ...................... 264/139 |
| 5,954,651 | A | 9/1999 | Berg et al. |
| 6,090,099 | A | 7/2000 | Samson et al. |
| 6,143,013 | A | 11/2000 | Samson et al. |
| 6,165,163 | A | 12/2000 | Chien et al. |
| 6,212,422 | B1 | 4/2001 | Berg et al. |
| 6,245,053 | B1 * | 6/2001 | Benjamin ................... 604/523 |
| 6,464,684 | B1 | 10/2002 | Galdonik |
| 6,505,066 | B2 | 1/2003 | Berg et al. |
| 6,591,472 | B1 * | 7/2003 | Noone et al. .................. 29/417 |
| 2004/0015150 | A1 * | 1/2004 | Zadno-Azizi ............... 604/523 |

FOREIGN PATENT DOCUMENTS

| | | |
|---|---|---|
| EP | 0 382 974 A1 | 8/1990 |
| EP | 0 473 045 A1 | 3/1992 |
| EP | 0 841 072 A2 | 5/1998 |
| EP | 1 123 714 A1 | 8/2001 |
| JP | 4-40652 | 4/1992 |
| JP | 5-84303 | 4/1993 |
| WO | WO 93/15785 A1 | 8/1993 |
| WO | WO 95/13110 A1 | 5/1995 |
| WO | WO 96/20750 A1 | 7/1996 |

OTHER PUBLICATIONS

Kolobow et al., "A New Thin-Walled Nonkinking Catheter for Peripheral Vascular Cannulation," *Surgery*, vol. 68, No. 4, Oct. 1970, pp. 625-626.

* cited by examiner

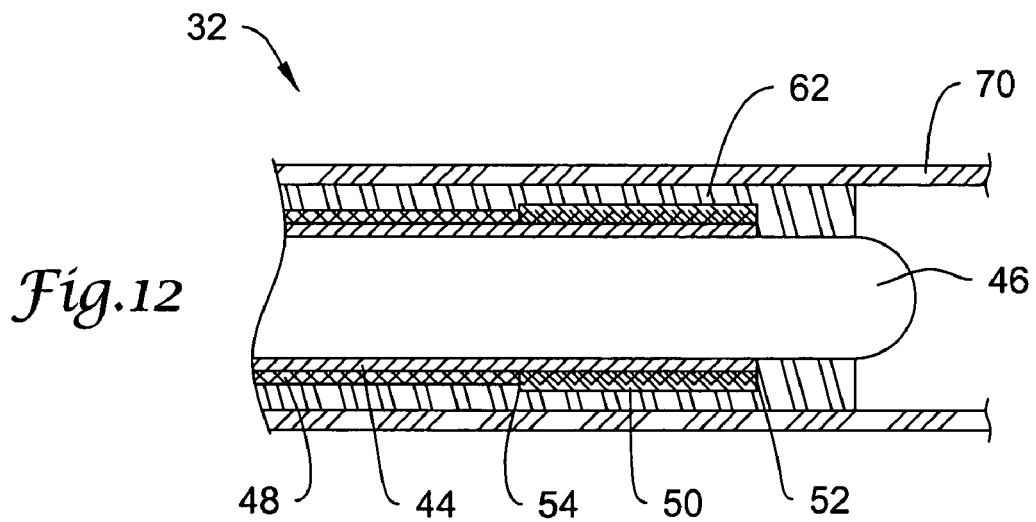
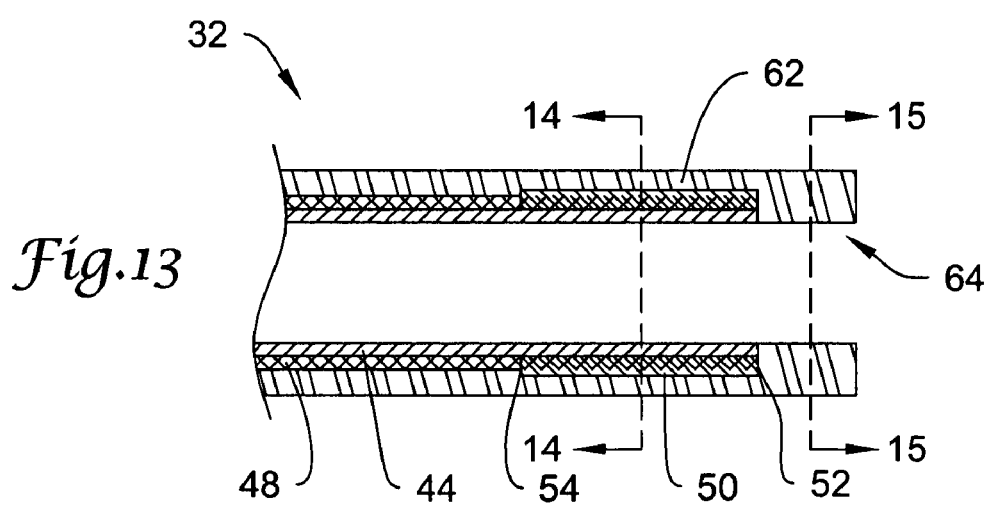
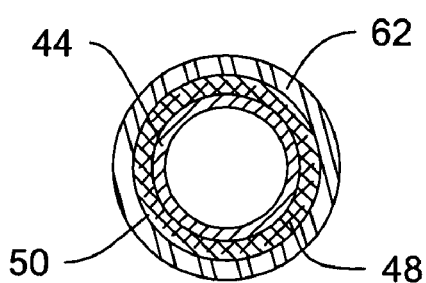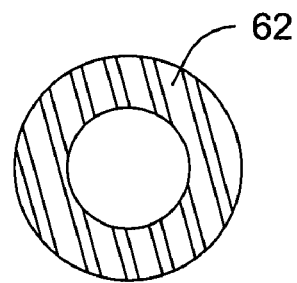

METHOD OF FORMING CATHETER DISTAL TIP

TECHNICAL FIELD

The invention relates generally to elongate medical devices and more particularly to catheters and methods of forming catheter distal tips.

BACKGROUND

Reinforcing layers such as reinforcing braid layers can provide thin-walled catheters with desired resistance to kinking while retaining desirable flexibility. Some reinforcing braids, such as tempered or high tensile stainless steel braids, can be susceptible to braid wire flaring in which unrestrained ends of the braid bend outward. Various techniques have been proposed for dealing with braid wire flaring, including the use of heat treatment processes on the braid, braid constraints and adhesives. Nevertheless, a need remains for improved methods of producing catheters having reinforcing braids while preventing or substantially preventing braid wire flaring without thickening the top layer or heat-treating the reinforcing braid material. A need also remains for a braid-reinforced catheter that has a well-bonded soft distal tip without use of adhesives.

SUMMARY

The invention is directed to catheters such as guide catheters that can include a reinforcing braid layer. Guide catheters can include distal tips such as atraumatic distal tips in which the reinforcing braid layer does not extend into the distal tip.

Accordingly, an example embodiment of the invention can be found in a method of forming a catheter. A braid layer is provided and a first polymer segment is secured over the braid layer. The first polymer segment can be positioned proximal of a distal end of the braid layer. The braid layer can be cut through at a cutting position that is proximate a distal end of the first polymer segment and the braid layer distal of the cutting position can be removed. A second polymer segment, that extends over the first polymer segment and that extends distally of the cutting position can be secured over the braid layer.

Another example embodiment of the invention can be found in a guide catheter that has a braid layer and an outer polymer layer and that is produced using a preferred process. A first polymer segment can be positioned over the braid layer and can be secured such that it is proximal of a distal end of the braid layer. The braid layer can be cut through at a cutting position that is proximate a distal end of the first polymer segment, and a portion of the braid layer that is distal of the cutting position can be removed. A second polymer segment that forms the outer polymer layer can be secured over the braid layer. The second polymer segment can extend over the first polymer segment and can extend distally of the cutting position.

Another example embodiment of the invention can be found in a guide catheter that includes an inner lubricious layer and a reinforcing braid layer that each extend proximally from a position proximal of a distal end of the catheter. An outer polymeric layer can extend proximally from the distal end of the catheter. A braid securement segment can extend proximally from a position proximal of the distal end of the catheter.

The braid securement segment can have a melting point that is lower than a melting point of the inner lubricious layer, but higher than a melting point of the outer polymeric layer. The braid securement segment can be melted into the braid layer, thereby preventing braid flaring during processing.

BRIEF DESCRIPTION OF THE FIGURES

FIG. 12 is a partial section view of the distal catheter shaft portion of FIG. 11 after applying heat to the heat shrink tube;

FIG. 13 is a partial section view of the distal catheter shaft portion of FIG. 12 illustrating the completed distal tip;

FIG. 14 is a cross-section view of FIG. 13 taken along line 14-14; and FIG. 15 is a cross-section view of FIG. 13 taken along line 15-15.

DETAILED DESCRIPTION

Figure 1:
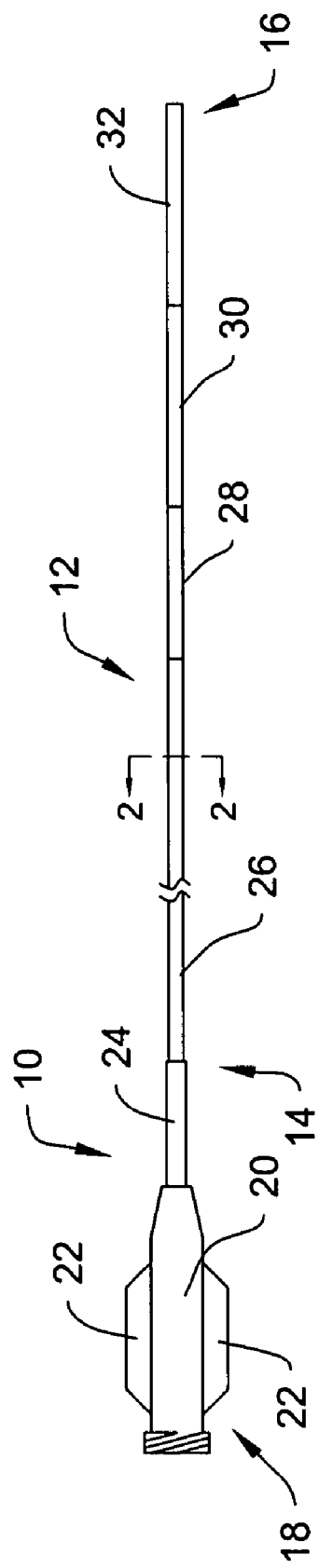
FIG. 1 is a plan view of a catheter in accordance with an embodiment of the invention.

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the present invention. The catheter 10 can be any of a variety of different catheters. In some embodiments, the catheter 10 can be an intravascular catheter. Examples of intravascular catheters include balloon catheters, atherectomy catheters, drug delivery catheters, diagnostic catheters and guide catheters. The intravascular catheter 10 can be sized in accordance with its intended use. The catheter 10 can have a length that is in the range of about 100 to 150 centimeters and can have any useful diameter. As illustrated, FIG. 1 portrays a guide catheter, but the invention is not limited to such. Except as described herein, the intravascular catheter 10 can be manufactured using conventional techniques.

In the illustrated embodiment, the intravascular catheter 10 includes an elongate shaft 12 that has a proximal end 14 and a distal end 16. A hub and strain relief assembly 18 can be connected to the proximal end 14 of the elongate shaft 12. The hub and strain relief assembly 18 includes a main body portion 20, a pair of flanges 22 designed to improve gripping and a strain relief 24 that is intended to reduce kinking. The hub and strain relief assembly 18 can be of conventional design and can be attached using conventional techniques. It is also recognized that alternative hub designs can be incorporated into embodiments of the present invention.

The elongate shaft 12 can include one or more shaft segments having varying degrees of flexibility. As illustrated, the elongate shaft 12 includes a first shaft segment 26, a second shaft segment 28 and a third shaft segment 30. In some embodiments, the elongate shaft 12 can include fewer shaft segments or only one shaft segment or can include more than three segments, depending on the flexibility requirements of a particular application.

Figure 2:
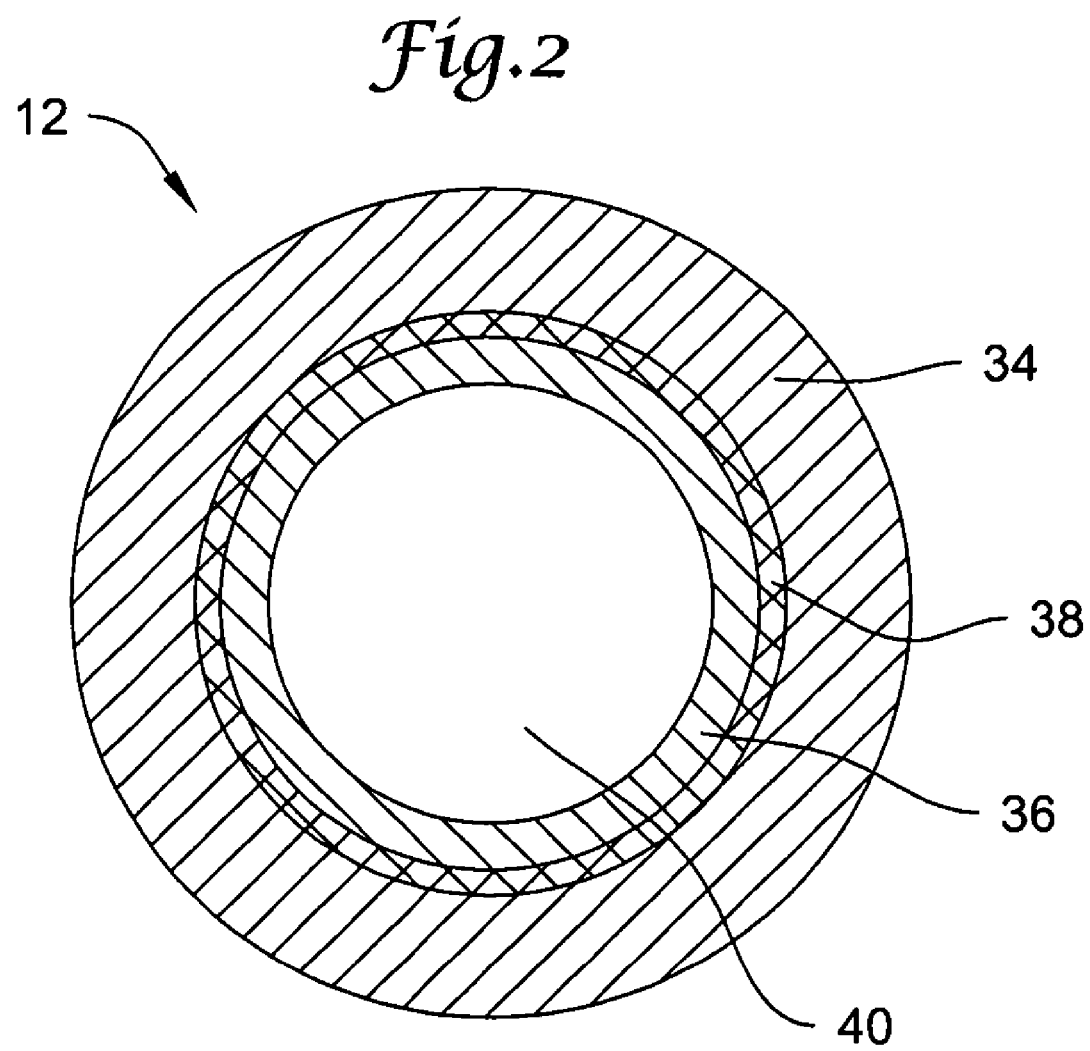
FIG. 2 is a cross-sectional view of the catheter of FIG. 1 taken along line 2-2.
Figure 4:
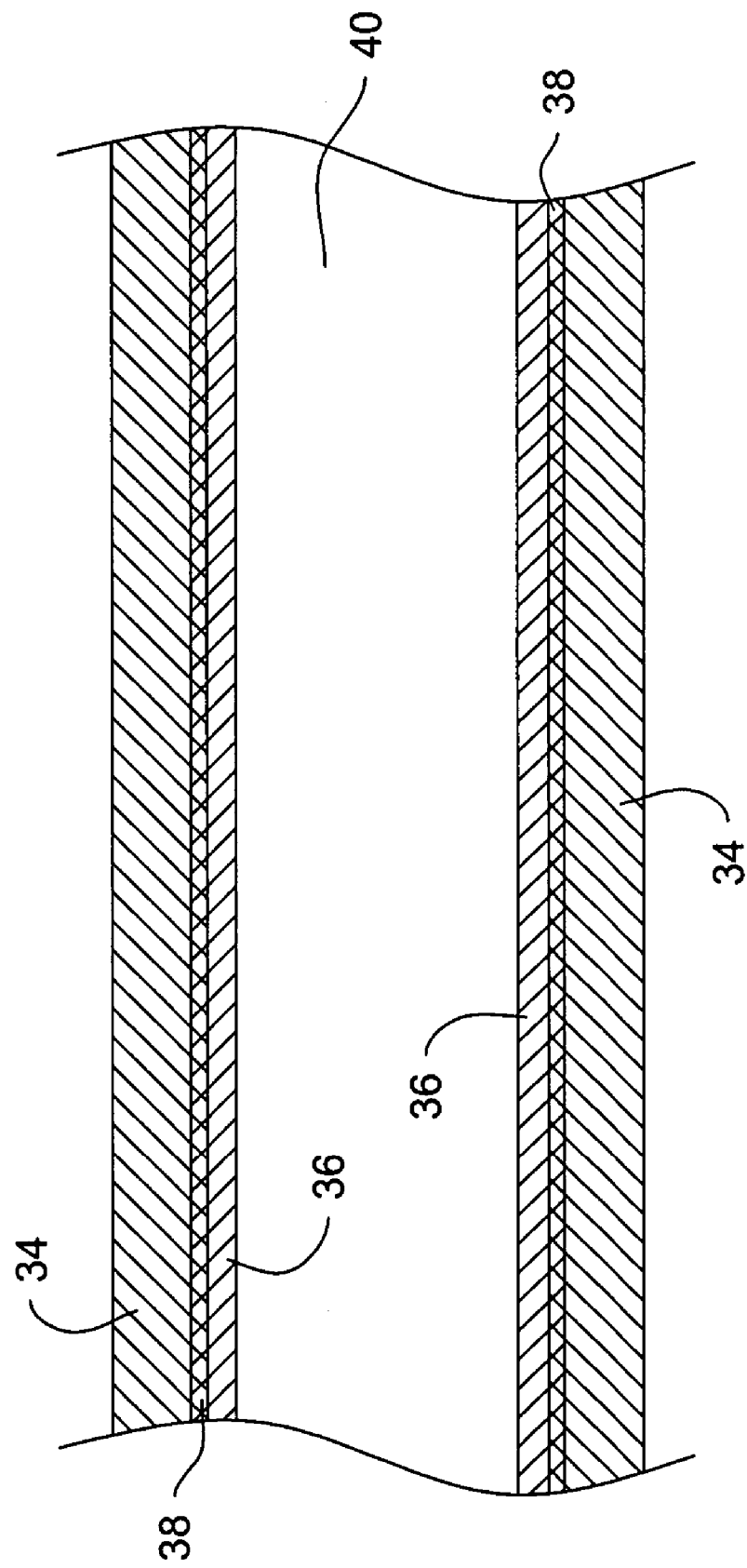
FIG. 4 is a partially sectioned view of the catheter of FIG. 1.

FIG. 2 is a cross-sectional view of the elongate shaft 12, taken along the line 2-2 of FIG. 1, while FIG. 4 is a cutaway view of the elongate shaft 12. The proximal portions of the elongate shaft 12, as illustrated, include an outer layer 34 and an inner layer 36, and can include a reinforcement layer 38 that is positioned between the inner layer 36 and the outer layer 34. The inner layer 36 defines a lumen 40 that extends through the elongate shaft 12. In some embodiments, the inner layer 36 can be omitted. The distal portion 32 of the elongate shaft 12 will be discussed in greater detail hereinafter.

Each of the shaft segments 26, 28, 30 can have a similar construction. In particular, each of the shaft segments 26, 28, 30 can include an inner layer 36 and a reinforcing layer 38 that is the same for or continuous through each of the shaft segments 26, 28, 30 and an outer layer 34 that becomes more flexible in the shaft segments 26, 28, 30 closest to the distal end 16 of the catheter 10. For example, the proximal shaft segment 26 can have an outer layer that is formed from a polymer having a hardness of 72 D (Durometer), the intermediate shaft segment 28 can have an outer layer having a hardness of 68 D and the distal shaft segment 30 can have an outer layer having a hardness of 46 D.

Each of the shaft segments 26, 28, 30 can be sized in accordance with the intended function of the resulting catheter 10. For example, the shaft segment 26 can have a length of about 35 inches, the shaft segment 28 can have a length in the range of about 2 to 3 inches and the shaft segment 30 can have a length in the range of about 1 to 1.25 inches.

The shaft segments 26, 28, 30 can be formed of any suitable material such as a polymeric material. Examples of suitable polymer material include any of a broad variety of polymers generally known for use as polymer sleeves. In some embodiments, the polymer material used is a thermoplastic polymer material. Some examples of some suitable materials include polyurethane, elastomeric polyamides, block polyamide/ethers, block polyethers/esters, silicones, and co-polymers. One preferred polymer is a polyurethane (PUR) and polyoxymethylene (POM or Delrin) blend.

In some embodiments, the inner layer 36 can be a single piece uniform material extending over the length of the shaft 12 and can define a lumen 40 that can run the entire length of the elongate shaft 12 and that is in fluid communication with a lumen (not illustrated) extending through the hub assembly 18. The lumen 40 defined by the inner layer 36 can provide passage to a variety of different medical devices or fluids, and thus the inner layer 36 can be manufactured from or include a lubricious material to reduce friction within the lumen 40. Examples of suitable materials include polytetrafluoroethylene (PTFE). The inner layer 36 can be dimensioned to define a lumen 40 having an appropriate inner diameter to accommodate its intended use. In some embodiments, the inner layer 36 can define a lumen 40 having a diameter of about 0.058 inches and can have a wall thickness of about 0.001 inches. A lubricious coating over the lumen wall of inner layer 36 can also be included.

In some embodiments, the outer layer 34 can include a portion made from a thermoplastic polymer such as a co-polyester thermoplastic polymer such as that available commercially under the ARNITEL® name. The use of an ARNITEL® polymer is described in detail below. The outer layer 34 can have an inner diameter that is about equal to the outer diameter of the inner layer 36. The outer layer 34 can have an inner diameter that is slightly greater than the outer diameter of the inner layer 36 to accommodate the thickness of the reinforcing braid layer 38. In some embodiments, the outer layer 34 can have an inner diameter in the range of about 0.0600 to about 0.0618 inches and an outer diameter in the range of about 0.0675 to about 0.0690 inches.

In some embodiments, the outer layer 34, or portions thereof, can include, or be filled with, radiopaque material to make the outer layer 34, or portions thereof, more visible when using certain imaging techniques, for example, fluoroscopy techniques. Any suitable radiopaque material known in the art can be used. Some examples include precious metals, tungsten, barium subcarbonate powder, and the like, and mixtures thereof. In some embodiments, the polymer can include different sections having different amounts of loading with radiopaque material. For example, the outer layer 34 can include a distal section having a higher level of radiopaque material loading, and a proximal section having a correspondingly lower level of loading.

Figure 3:
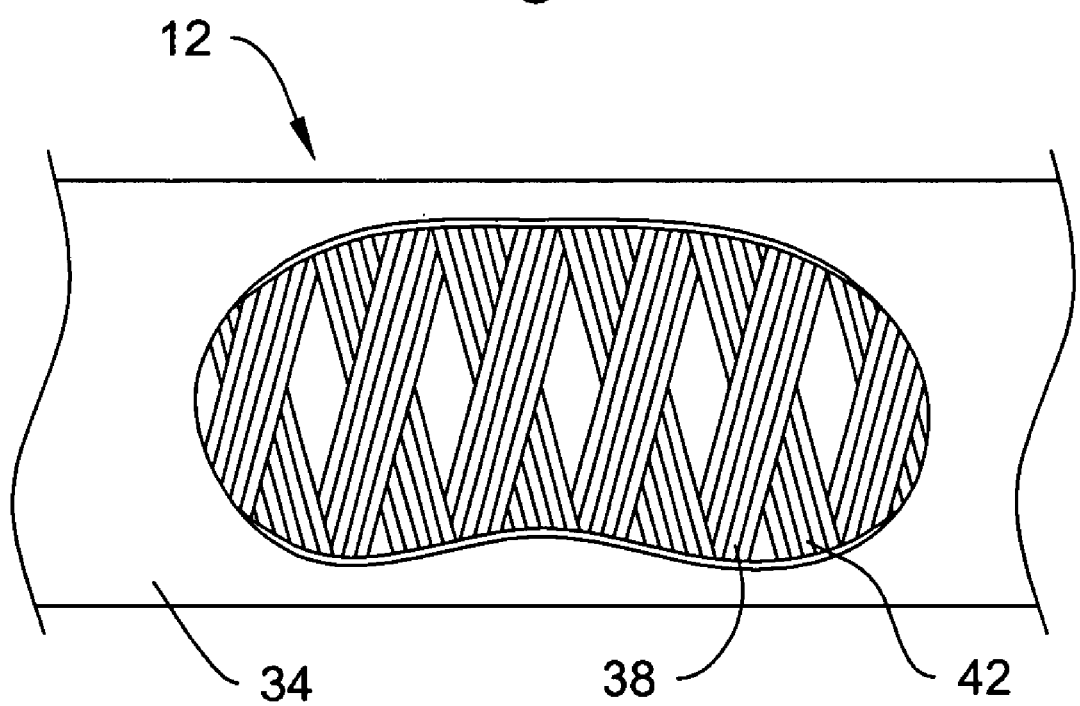
FIG. 3 is a partially sectioned view of the catheter of FIG. 1 illustrating an example braid pattern.

A reinforcing braid layer 38 can be positioned between the inner layer 36 and the outer layer 34. With reference to FIG. 3, the reinforcing braid layer 38 can be formed of any suitable material, including metals and metal alloys. In some embodiments, the reinforcing braid layer 38 can include a metal wire braid formed of stainless steel, tungsten, gold, titanium, silver, copper, platinum, molybdenum or iridium. The reinforcing braid layer 38 can also be formed from non-metallic material such as KEVLAR® (poly paraphenylene terephthalamide) fibers, LCP (liquid crystal polymer) fibers or glass fibers. In some embodiments, the reinforcing braid layer 38 can be formed of a high tensile stainless steel.

In at least some embodiments, portions or all of the reinforcing braid layer 38 can include a radiopaque material. Some examples of radiopaque materials can include, but are not limited to, gold, platinum, palladium, tantalum, tungsten alloy, polymer material loaded with a radiopaque filler, and the like.

In some embodiments, a degree of MRI compatibility can be imparted. For example, to enhance compatibility with Magnetic Resonance Imaging (MRI) machines, it may be desirable to make the reinforcing braid layer 38, or other portions thereof, in a manner that would impart a degree of MRI compatibility. For example, the reinforcing braid layer 38, or portions thereof, may be made of a material that does not substantially distort the image and create substantial artifacts, which are gaps in the image. Certain ferromagnetic materials, for example, may not be suitable because they may create artifacts in an MRI image. The reinforcing braid layer 38, or portions thereof, may also be made from a material that the MRI machine can image. Some materials that exhibit these characteristics include, for example, tungsten, Elgiloy, MP35N, nitinol, and the like, and others.

In some embodiments, the reinforcing braid layer 38 can be formed of a plurality of individual fibers 42. The individual fibers 42 can be flat or round or other shapes (D-shaped, triangle, etc.) in cross-section and can be woven together in a variety of patterns. As illustrated, the fibers 42 are woven together in a three-over-three pattern, while any other patterns such as a four-over-four pattern or even a five-over five pattern or a two over four pattern can also be used. In particular, the fibers 42 can be formed of wire having a round cross-section and a diameter of about 0.001 inches.

An intravascular catheter 10 can optionally include a coating layer such as a lubricious coating layer over part or all of the catheter 10. Suitable lubricious polymers are well known in the art and can include hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Certain hydrophobic coatings such as PTFE, silicone coatings, etc., can also be utilized.

The distal portion 32 of the elongate shaft 12 is described, for example, in FIGS. 5 through 12, which illustrate an exemplary method of forming the distal portion 32, as well as FIGS. 13-15, which illustrate the finished distal portion 32 of the elongate shaft 12.

Figure 5:
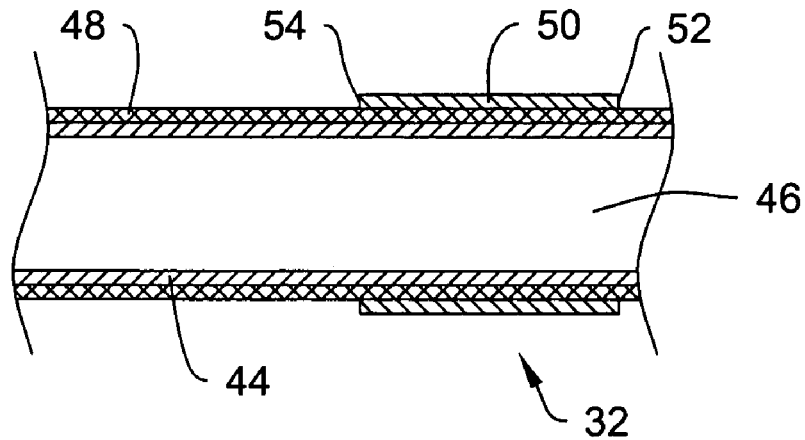
FIG. 5 is a partial sectional view of a distal portion of a catheter shaft showing a liner, reinforcing braid and braid securement segment in accordance with an embodiment of the invention.
Figure 6:
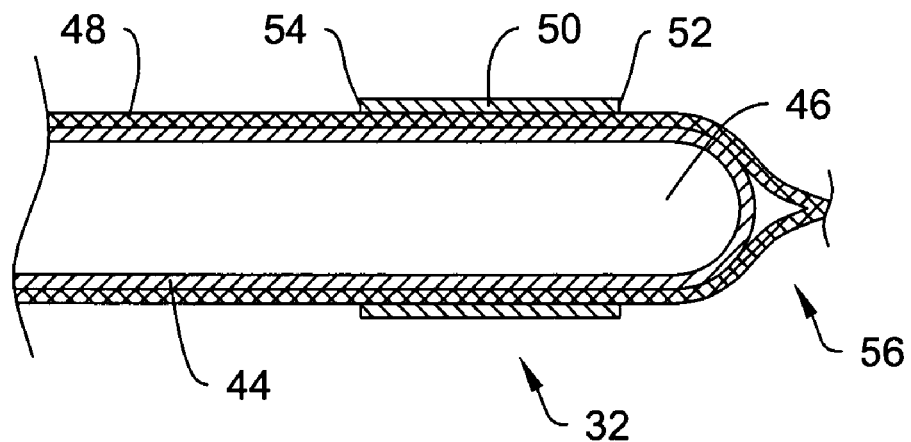
FIG. 6 is a partial section view of an alternative embodiment of the distal portion of a catheter shaft of FIG. 5.

In an example method of forming the distal portion 32, FIGS. 5 and 6 show an optional inner liner 44 positioned over a mandrel 46. In some embodiments, the inner liner 44 can represent a distal portion of the inner liner 36 discussed with respect to the more proximal portions of the elongate shaft 12. A reinforcing braid layer 48 having a distal end 56 (FIG. 6) has been positioned over the inner liner 44. In some embodiments, the reinforcing braid layer 48 can represent a distal portion of the reinforcing braid layer 38 discussed with respect to the more proximal portions of the elongate shaft.

A braid securement segment 50 can be positioned over the reinforcing braid layer 48. The braid securement segment 50 can have a distal end 52 and a proximal end 54, and the braid securement segment 50 can be positioned such that the reinforcing braid layer 48 extends distally beyond the distal end 52 of the braid securement segment 50.

The inner layer 44 can be formed of any suitable polymer as discussed above. In some embodiments, the inner layer 44 can be formed of a fluoropolymer such as polytetrafluoroethylene (PTFE). The reinforcing braid layer 48 can be formed of any suitable reinforcing material. In some embodiments, the reinforcing braid layer 48 can be formed of high tensile stainless steel.

The braid securement segment 50 can be formed of any suitable polymer as discussed previously. It can be advantageous for the braid securement segment 50 to be formed of a polymer that has a melting point that is less than that of the inner layer 44. In some embodiments, the braid securement segment 50 can be formed of a polyether-ester polymer having a melting point of greater than about 400° F. ARNITEL PL380, which is a suitable example of such a polymer, has a melting point of about 413° F.

The braid securement segment 50 can be dimensioned as appropriate for the particular catheter being formed. In some embodiments, the braid securement segment 50 can have a length that is in the range of about 0.1 to about 40 inches and a wall thickness that is in the range of about 0.0005 to about 0.006 inches.

In positioning and subsequently securing the braid securement segment 50, it can be advantageous to prevent the distal end 56 of the braid securement segment 50 from flaring. In some embodiments, as illustrated for example in FIG. 5, this can be accomplished at least in part by extending the reinforcing braid layer 48 distally of where the braid securement segment 50 is being attached. It has been found that when a reinforcing braid made from a high tensile material such as high tensile stainless steel flares, typically only the ends of the braid will flare. Thus, it can be beneficial but not necessary to extend the reinforcing braid layer 48 a distance of about 0.1 inches or more distally beyond the braid securement segment 50.

In some embodiments, as illustrated for example in FIG. 6, it can be advantageous to secure the distal end 56 of the reinforcing braid layer 48 at a position distal of the braid securement segment 50. This can be accomplished using any suitable mechanical means of securement, such as twisting individual elements of the distal end 56 of the reinforcing braid layer 48 together, or soldering or otherwise adhering the individual elements of the distal end 56 together.

Figure 7:
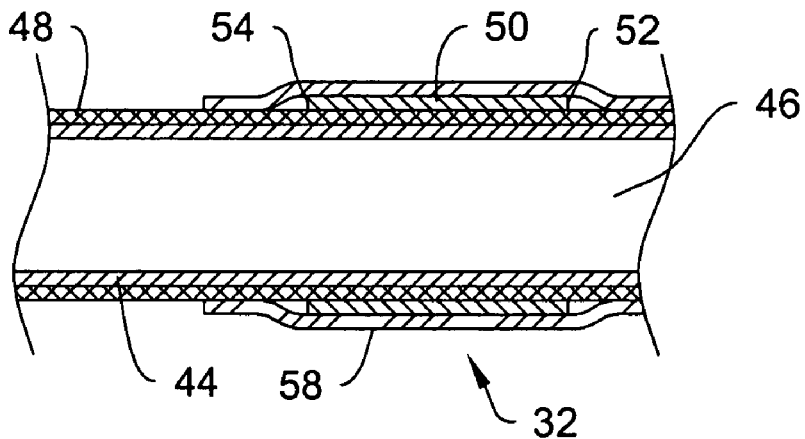
FIG. 7 is a partial section view of the distal catheter shaft portion of FIG. 5 showing the addition of a heat shrink tube.
Figure 8:
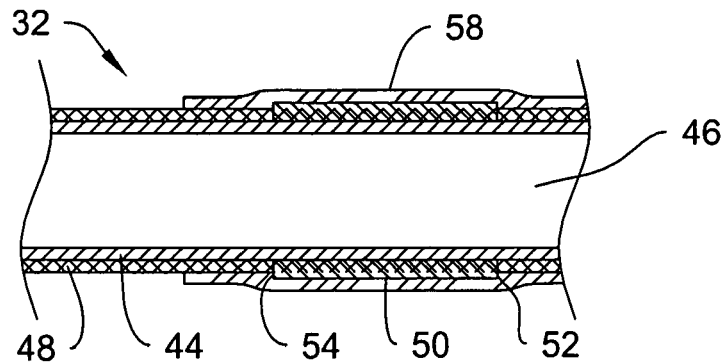
FIG. 8 is a partial section view of the distal catheter shaft portion of FIG. 7 after applying heat to the heat shrink tube covered assembly.

Once the braid securement segment 50 has been positioned over the reinforcing braid layer 48, it can be secured thereon using any suitable method, preferably heat and pressure. In some embodiments, as illustrated for example in FIGS. 7 and 8, a heat shrink tube 58 can be positioned over the braid securement segment 50. FIG. 7 shows the heat shrink tube 58 prior to applying sufficient heat to shrink the heat tube 58, while FIG. 8 shows the heat shrink tube 58 after sufficient heat has been applied to at least partially melt the braid securement segment 50 into or to conform with the reinforcing braid layer 48.

The heat shrink tube 58 can be formed of any suitable heat shrink polymer known in the art. In some embodiments, it can be beneficial to use a heat shrink polymer that has a melting point that is above that of the braid securement segment 50. In some particular embodiments, the heat shrink tube 58 can be formed of a fluoropolymer such as a perfluoro (ethylene-propylene) copolymer having a melting point of at least about 500° F.

Figure 9:
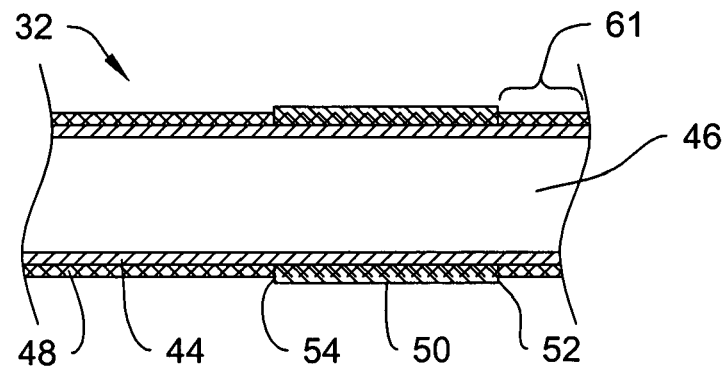
FIG. 9 is a partial section view of the distal catheter shaft portion of FIG. 8 after removing the heat shrink tube.

FIG. 9 illustrates the distal portion 32 after the heat shrink tube 58 has been removed. As illustrated, the braid securement segment 50 has been at least partially melted into or conformed to the reinforcing braid layer 48. As a result, the braid securement segment 50 can at least substantially prevent flaring during subsequent processing steps.

Figure 10:
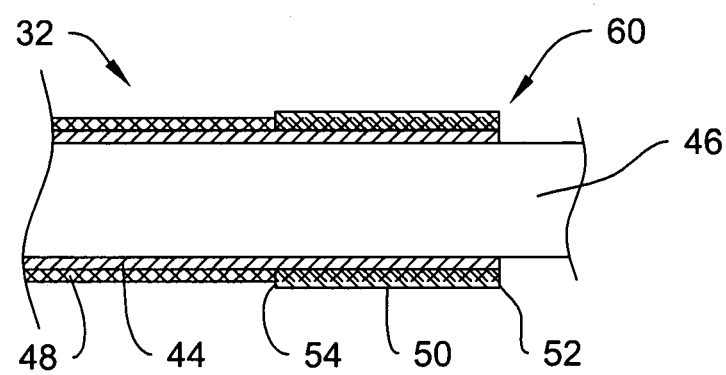
FIG. 10 is a partial section view of the distal catheter shaft portion of FIG. 9 after cutting through the braid and liner at the distal end of the braid securement segment.

Processing continues as illustrated in FIG. 10, in which the inner liner 44 (if present) and the reinforcing braid layer 48 are cut through at a cutting position 60. Cutting can be accomplished using any suitable method, including mechanical shearing or ablative techniques such as a laser. In some embodiments, the cutting position 60 can be proximate the distal end 52 of the braid securement segment 50. The portions 61 of the inner liner 44 and the reinforcing braid layer 48 that extend distally of the cutting position 60 can be removed.

Figure 11:
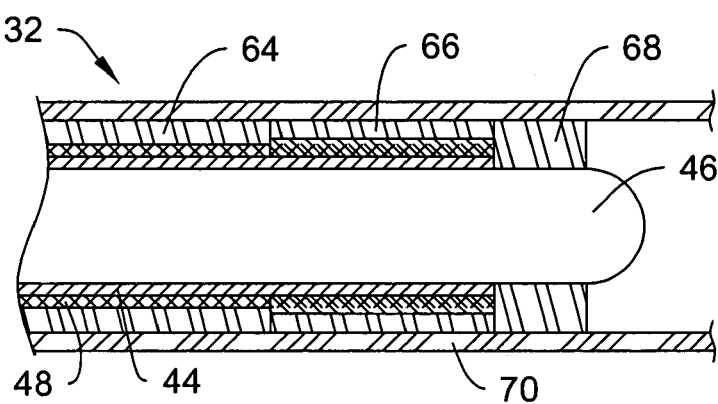
FIG. 11 is a partial section view of the distal catheter shaft portion of FIG. 10 after positioning segments of the outer polymer layer and a heat shrink tube.

FIGS. 11-12 illustrate a particular method of forming the outer layer 62, shown for example in FIG. 13. The outer layer 62 can be formed of any suitable polymer. In one embodiment, the outer layer 62 is formed of a polymer that has a melting point that is below that of the braid securement segment 50. As a result, thermal processing of the outer layer 62 (as described hereinafter) will have little or no effect on the braid securement segment 50, and thus the reinforcing braid layer will exhibit substantially no flaring.

The outer layer 62 can be formed from a single polymer tube, or a plurality of individual segments. In some illustrated embodiments, the outer layer 62 can be formed from a proximal segment 64 that is configured to overlay the reinforcing layer 48, an intermediate segment 66 that is configured to overlay the braid securement segment 50, and a distal segment 68 that is configured to form a distal tip. Each of the proximal segment 64, the intermediate segment 66 and the distal segment 68 can be formed from the same material, or each can be different. Alternatively, segments of polymer materials may be blended with other polymers or different materials.

In some embodiments, each of the proximal segment 64, the intermediate segment 66 and the distal segment 68 can be formed of the same material, but of differing mechanical characteristics. In some embodiments, the outer layer 62 can be formed of a polymer that has a melting point that is below about 400° F., and in particular embodiments, the outer layer 62 can be formed of a polymer such as an acetal resin/polyurethane blend that has a melting point of about 350° F. A preferred polymer is a polyoxymethylene and polyurethane blend.

Each of the proximal segment 64, the intermediate segment 66 and the distal tip 68 can be secured using any suitable method, preferably heat and pressure. In some embodiments, as illustrated for example in FIGS. 11 and 12, a heat shrink tube 70 can be used. In some embodiments, sufficient heat is applied to melt the proximal segment 64, the intermediate segment 66 and the distal segment 68 without melting or excessively softening the braid reinforcement segment 50.

FIG. 11 shows the heat shrink tube 70 prior to applying sufficient heat to shrink the heat tube 70 while FIG. 12 shows the heat shrink tube 70 after sufficient heat has been applied. The heat shrink tube 70 can be formed of any suitable material, such as those discussed with respect to the heat shrink tube 58.

In some embodiments, as illustrated for example in FIGS. 12-15, the proximal segment 64, the intermediate segment 66 and the distal segment 68 are all formed of the same polymer and can form a continuous outer layer 62 after heat shrinking. In particular, FIG. 13 shows a distal portion 32 having a continuous outer layer 62. The outer layer 62 includes a distal tip 64 that is free of any reinforcing braid layer 48 or inner layer 44 and thus can provide a suitable level of flexibility.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

I claim:

1. A method of forming a catheter, comprising:
providing a braid layer having a distal end and a proximal end, an inner lubricious liner positioned within the braid layer;
securing a first polymer segment over the braid layer, the first polymer segment being positioned proximal of the distal end of the braid layer, the first polymer segment having a distal end and a proximal end;
cutting through the braid layer and the inner lubricious liner at a cutting position proximate the distal end of the first polymer segment and removing a portion of the braid layer that extends distally of the cutting position; and
subsequent to cutting through the braid layer and the inner lubricious liner, securing a second polymer segment over the braid layer, the second polymer segment being positioned such that a proximal end of the second polymer segment is proximal the distal end of the first polymer segment and a distal end of the second polymer segment extends distally of the cutting position,
wherein the second polymer segment comprises in combination a proximal segment configured to overlay the braid layer, an intermediate segment configured to overlay the first polymer segment, and a distal segment configured to form a distal tip.

2. The method of claim 1, wherein the first polymer segment has a melting point that is at least about 10° F. above a melting point of the second polymer segment.

3. The method of claim 1, wherein securing the first polymer segment comprises positioning a heat shrink tube over the first polymer segment and applying sufficient heat and pressure to melt the first polymer segment.

4. The method of claim 1, wherein securing the second polymer segment comprises positioning a heat shrink tube over the second polymer segment and applying sufficient heat and pressure to melt the second polymer segment but not enough heat to melt the first polymer segment.

5. The method of claim 4, wherein the first polymer segment has a melting point that is greater than about 400° F. and the second polymer segment has a melting point that is less than about 400° F.

6. The method of claim 4, wherein the second polymer segment has a melting point that is about 350° F.

7. The method of claim 1, wherein the first polymer segment comprises a polyether-ester elastomer.

8. The method of claim 1, wherein the second polymer segment comprises an acetal resin/polyurethane blend.

9. The method of claim 3, wherein the heat shrink tube comprises a perfluoro (ethylene-propylene) copolymer.

10. The method of claim 4, wherein the heat shrink tube comprises a perfluoro (ethylene-propylene) copolymer.

11. The method of claim 1, wherein providing the braid layer comprises providing a braid layer that extends sufficiently distally of the cutting position to substantially prevent braid flaring at the cutting position.

12. A method of forming a catheter, comprising:
providing a braid layer having a distal end and a proximal end;
positioning an inner lubricious liner within the braid layer;
securing a first polymer segment over the braid layer, the first polymer segment being positioned proximal of the distal end of the braid layer;
cutting through the braid layer at a cutting location proximal of the distal end of the braid layer, thereby forming a catheter sub-assembly including the inner lubricious liner, the braid layer, and the first polymer segment, the catheter sub-assembly having a distal end defined at the cutting location;

securing a second polymer segment over the catheter sub-assembly, the second polymer segment being positioned such that a proximal end of the second polymer segment is proximal the cutting location and a distal end of the second polymer segment extends distally of the distal end of the catheter sub-assembly; and forming a portion of the polymeric outer segment into a distal tip for the catheter that is free from the lubricious layer and the braid layer, wherein the step of securing the second polymer segment over the catheter sub-assembly is performed subsequent to the step of cutting through the braid layer.

13. The method of claim 12, wherein the first polymer segment prevents flaring of the braid layer consequent cutting through the braid layer.

* * * * *

UNITED STATES PATENT AND TRADEMARK OFFICE
CERTIFICATE OF CORRECTION

PATENT NO. : 7,597,830 B2  Page 1 of 1
APPLICATION NO. : 10/615651
DATED : October 6, 2009
INVENTOR(S) : Pu Zhou It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Twenty-eighth Day of September, 2010

David J. Kappos
*Director of the United States Patent and Trademark Office*